United States Patent
Beck et al.

(10) Patent No.: US 12,408,873 B2
(45) Date of Patent: Sep. 9, 2025

(54) SETTING A POSITION OF A PATIENT TABLE OR AN OBJECT POSITIONED ON THE PATIENT TABLE

(71) Applicant: Siemens Healthineers AG, Forchheim (DE)

(72) Inventors: Thomas Beck, Dormitz (DE); Sven Helmecke, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 41 days.

(21) Appl. No.: 18/229,998

(22) Filed: Aug. 3, 2023

(65) Prior Publication Data
US 2024/0041409 A1    Feb. 8, 2024

(30) Foreign Application Priority Data
Aug. 5, 2022  (EP) .................................. 22189025

(51) Int. Cl.
*A61B 5/00* (2006.01)
*A61B 5/055* (2006.01)

(52) U.S. Cl.
CPC .............. *A61B 5/704* (2013.01); *A61B 5/055* (2013.01); *A61B 5/706* (2013.01); *A61B 5/7475* (2013.01); *A61B 2562/0257* (2013.01)

(58) Field of Classification Search
CPC ......... A61B 5/704; A61B 5/055; A61B 5/706; A61B 5/7475; A61B 2562/0257
See application file for complete search history.

(56) References Cited

U.S. PATENT DOCUMENTS

| | | |
|---|---|---|
| 2005/0025706 A1 | 2/2005 | Kagermeier |
| 2016/0073979 A1 | 3/2016 | Braun et al. |
| 2016/0202864 A1* | 7/2016 | Hardie .................. G06F 3/0484 715/771 |
| 2016/0274782 A1* | 9/2016 | Keil ....................... A61B 5/7435 |
| 2018/0325415 A1* | 11/2018 | Ehrl ........................ G06T 7/246 |

FOREIGN PATENT DOCUMENTS

| | | |
|---|---|---|
| DE | 10334073 A1 | 2/2005 |
| DE | 102007017794 B3 | 12/2008 |
| DE | 102014218557 A1 | 3/2016 |

* cited by examiner

Primary Examiner — Joel F Brutus
(74) Attorney, Agent, or Firm — Banner & Witcoff Ltd.

(57) ABSTRACT

Magnetic resonance (MR) apparatus and a monitoring unit, wherein the MR apparatus includes: a scanner unit to acquire medical MR data; a patient receiving region surrounded at least in part by the scanner unit; a patient positioning apparatus having a patient table designed to be movable into the patient receiving region; a position acquisition unit to acquire position data of a position of the patient table and/or of an object positioned on the patient table, wherein the position acquisition unit comprises a camera; and a setting unit operable, based on a provided setting parameter, to set the position of the patient table and/or of the object on the patient table, wherein the monitoring unit is designed so as, with the acquired position data, to provide the setting parameter for setting a position of the patient table and/or of the object on the patient table.

13 Claims, 2 Drawing Sheets

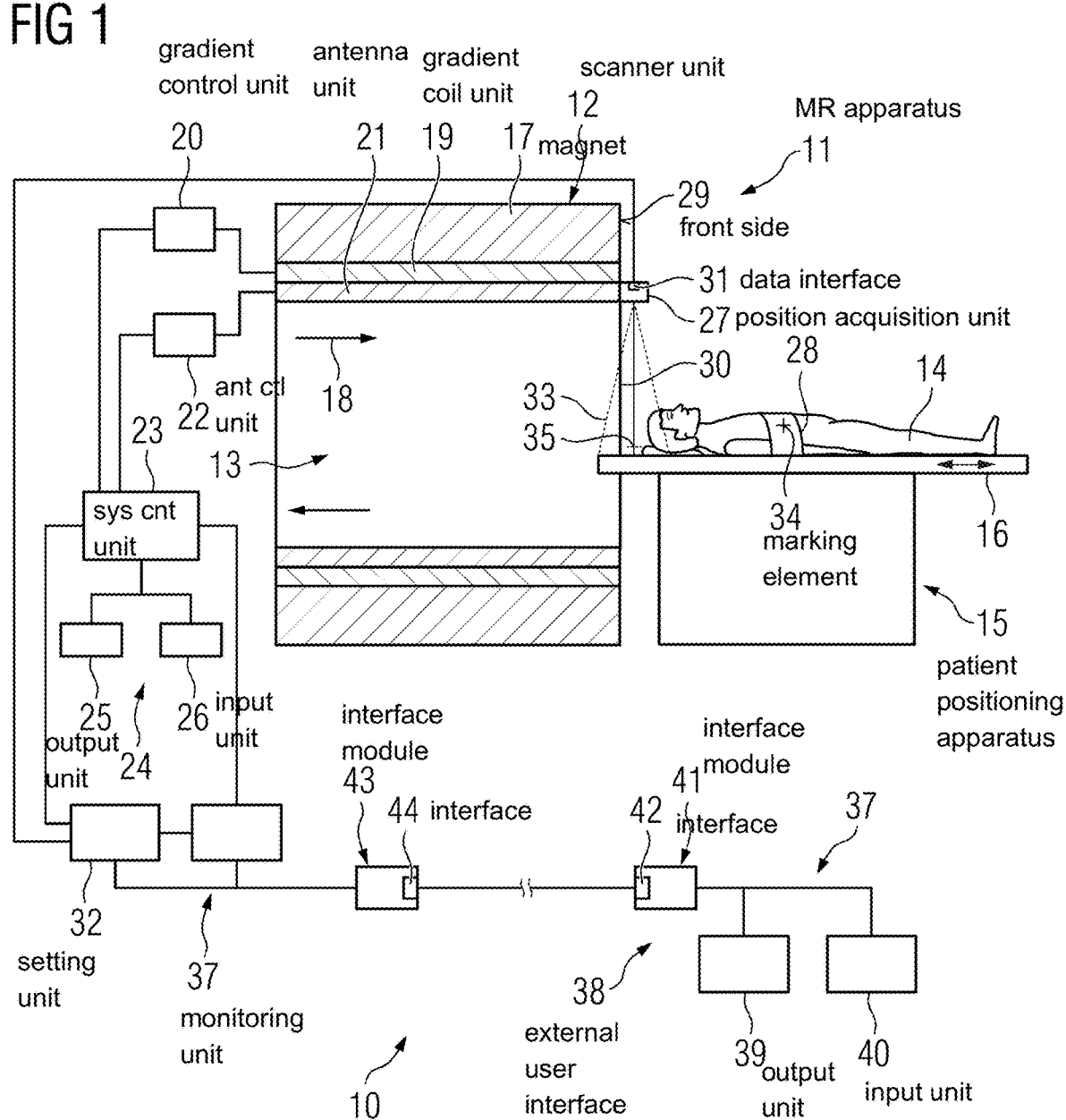

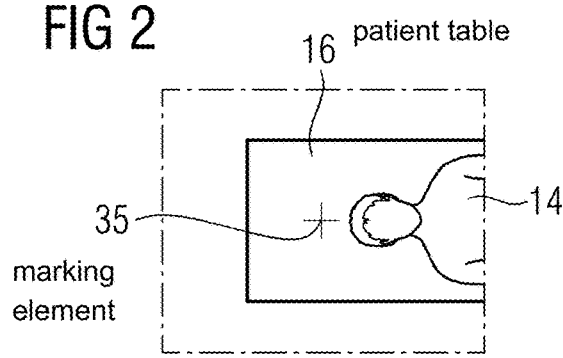
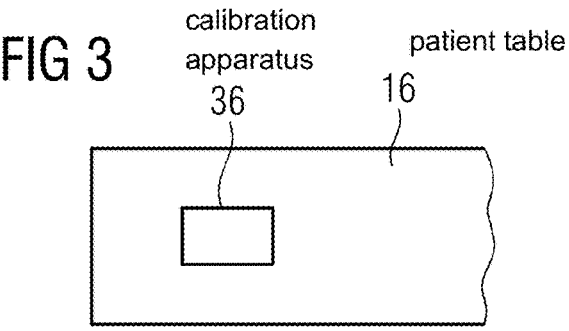
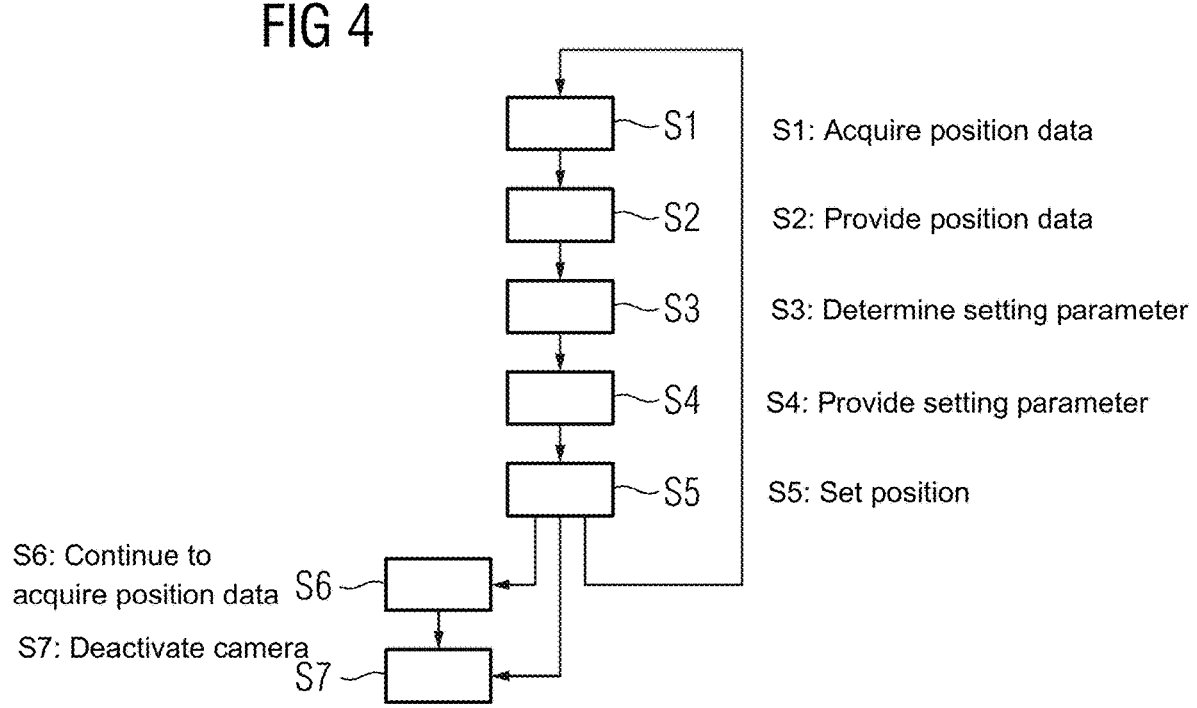

SETTING A POSITION OF A PATIENT TABLE OR AN OBJECT POSITIONED ON THE PATIENT TABLE

TECHNICAL FIELD

The present disclosure relates to a system comprising a magnetic resonance apparatus and an external user interface, wherein the system is designed so as to set a positioning of a patient table and/or of an object that is positioned on the patient table. Furthermore, the disclosure relates to a method for setting a position of a patient table and/or of an object that is positioned on the patient table. Moreover, the disclosure relates to a computer program product which comprises a program in order to perform the method for setting a position of a patient table and/or of an object that is positioned on the patient table. In addition, the disclosure relates to an electronically readable data carrier having the computer program.

BACKGROUND

For a magnetic resonance examination, the patient is initially positioned on a patient positioning apparatus, in particular a patient table of the patient positioning apparatus, and subsequently the patient table together with the patient is brought into and/or moved into a patient receiving region of the magnetic resonance apparatus. As is known, magnetic resonance apparatuses have for this purpose a laser marker that is arranged above an insertion opening of the patient receiving region. The laser marker renders it possible to define and/or mark the region of the patient that is to be examined. In this case, the patient table is manually displaced until the relevant region and/or the region that is to be examined is arranged in the focus of the laser marker. Subsequently, the patient table is automatically moved into the patient receiving region, wherein the position that is marked by means of the laser marker is arranged in the isocenter of the magnetic resonance apparatus. However, it is often difficult for an untrained and/or inexperienced operator to position the patient table manually into the correct position for marking.

SUMMARY

An object of the present disclosure is in particular to simplify a positioning of the patient table within the patient receiving region for a user. The object is achieved by means of the features of the independent claims. Advantageous embodiments are described in the subordinate claims.

The disclosure is based on a system comprising a magnetic resonance apparatus and a monitoring unit,
  wherein the magnetic resonance apparatus comprises:
    a scanner unit that is designed so as to acquire medical magnetic resonance data,
    a patient receiving region that is surrounded at least in part by the scanner unit,
    a patient positioning apparatus having a movable patient table, wherein the patient table is designed in such a manner that it can be moved into the patient receiving region,
    a position acquisition unit that is designed so as to acquire position data of a position of the patient table and/or of an object that is positioned on the patient table, wherein the position acquisition unit comprises a camera, and
    a setting unit that is designed so as, with the aid of a provided setting parameter, to set the position of the patient table and/or of the object that is positioned on the patient table,
  wherein the monitoring unit is designed so as, with the aid of the acquired position data, to provide a setting parameter for setting a position of the patient table and/or of the object that is positioned on the patient table.

It is preferred that the magnetic resonance apparatus comprises a medical and/or diagnostic magnetic resonance apparatus which is configured and/or designed so as to acquire medical and/or diagnostic image data, in particular medical and/or diagnostic magnetic resonance image data, of a patient. It is preferred that the scanner unit of the magnetic resonance apparatus comprises a detector unit, in particular a magnet unit, for acquiring the medical and/or diagnostic image data, in particular magnetic resonance image data. In so doing, the scanner unit, in particular the magnet unit, comprises a basic magnet, a gradient coil unit and a high-frequency antenna unit. The high-frequency antenna unit is arranged in this case fixedly within the scanner unit. In addition, the magnetic resonance apparatus can also comprise local high-frequency coils that are arranged around the region of a patient that is to be examined so as to acquire magnetic resonance data.

The basic magnet is designed so as to generate a homogeneous basic magnetic field having a defined magnetic field strength, such as for example having a magnetic field strength of 0.55 T or 1.5 T or 3 T or 7 T etc. In particular, the basic magnet is designed so as to generate a strong, constant and homogeneous basic magnetic field. It is preferred that the homogeneous basic magnetic field is arranged and/or located within a patient receiving region of the magnetic resonance apparatus. The gradient system is designed so as to generate magnetic field gradients that are used for position encoding during imaging.

Fora magnetic resonance examination, the patient, in particular the region of the patient that is to be examined, is positioned within a patient receiving region of the magnetic resonance apparatus. In this case, the patient receiving region is surrounded at least in part by the scanner unit, in particular is surrounded in a cylindrical manner by the scanner unit. It is preferred that a field of view (FOV) and/or an isocenter of the magnetic resonance apparatus is arranged within the patient receiving region. It is preferred that the FOV comprises an acquisition region of the magnetic resonance apparatus, within which the conditions for acquiring medical image data, in particular magnetic resonance image data, are present within the patient receiving region, such as for example a homogeneous basic magnetic field. It is preferred that the isocenter of the magnetic resonance apparatus comprises the region and/or the point within the magnetic resonance apparatus that has the optimum and/or ideal conditions for acquiring medical image data, in particular magnetic resonance image data. In particular, the isocenter comprises the most homogeneous magnetic field region within the magnetic resonance apparatus.

For a positioning of the patient, in particular of the region of the patient that is to be examined, within the patient receiving region the magnetic resonance apparatus has a patient positioning apparatus. The patient positioning apparatus is designed so as to orient and/or position the patient for a magnetic resonance examination of the patient. It is preferred that the patient positioning apparatus has a movable patient table that is designed so as to be able to be moved in particular within the patient receiving region of the magnetic resonance apparatus. For a magnetic resonance examination, the patient is initially positioned on the patient table of the patient positioning apparatus and subsequently the patient table is moved together with the patient into the patient receiving region until the region of the patient that is to be examined is positioned within the isocenter.

The object that is positioned on the patient table can comprise for example a patient, in particular the region of the patient that is to be examined. In addition, the object that is positioned on the patient table can also comprise an auxiliary unit, such as for example a local high-frequency coil, which is arranged for a medical and/or diagnostic magnetic resonance examination around the patient, in particular around the region of the patient that is to be examined. Furthermore, the object that is positioned on the patient table can comprise, for example, for calibration measurements a phantom etc.

It is preferred that the position acquisition unit is designed so as to acquire a position of the patient table and/or of the object that is positioned on the patient table. It is preferred in this case that the position of the patient table and/or of the object that is positioned on the patient table can be acquired with respect to a reference position and/or with regard to the isocenter of the scanner unit. It is preferred that the position acquisition unit comprises a camera. It is preferred that the position data comprise in this case camera data and in particular advantageously video data. In so doing, it is preferred that the position acquisition unit, in particular the camera, has a detecting region and/or a field of view that is directed at a region directly in front of the insertion opening of the patient receiving region.

For a positioning of the patient table and/or of the object that is positioned on the patient table in the patient receiving region, in particular in the isocenter of the magnetic resonance apparatus, firstly the patient table and/or the object that is positioned on the patient table, in particular a region of the patient table and/or of the object that is positioned on the patient table that is relevant for the imminent examination, is positioned in a reference position that preferably comprises a center point in the field of view of the camera. It is preferred that the position acquisition unit, in particular the camera, is designed in such a manner that this reference position is marked in the acquired position data, for example by a crosshair. For this positioning of the patient table and/or of the object that is positioned on the patient table in this reference position, position data is acquired by means of the position acquisition unit, in particular by means of the camera. This reference position has a defined distance from the isocenter of the magnetic resonance apparatus with the result that after a positioning of the patient table and/or the object on the patient table, in particular a region of the patient table and/or of the object that is positioned on the patient table that is relevant for the imminent examination, is positioned in this reference position, the patient table or the patient table together with the object that is positioned on the patient table can be positioned rapidly and simply in the isocenter. In addition, for the positioning, it is possible for the patient table and/or the object that is positioned on the patient table, in particular a region of the patient table and/or of the object that is positioned on the patient table that is relevant for the imminent examination, to have a marking.

The setting unit of the magnetic resonance apparatus is designed so as to set a position of the patient table or of the patient table together with the object that is positioned on the patient table. It is preferred that the setting unit has for this purpose a drive unit which generates a drive torque for a movement of the patient table. In addition, the setting unit can also comprise a computing module and/or a processor in order to control a movement of the patient table. Furthermore, the setting unit can also comprise appropriate software and/or computer programs for controlling a movement and/or a positioning of the patient table. It is preferred that the setting parameter comprises a parameter for controlling a movement of the patient table. For example, it is possible by means of the setting parameter to set and/or control a direction and/or a speed of a movement of the patient table. In addition, the setting parameter can also comprise a stop parameter that causes the movement of the patient table to stop, for example if the patient table is arranged within the reference position or also in a dangerous situation.

The monitoring unit is designed so as, with the aid of the acquired position data, to provide a setting parameter for setting a position of the patient table and/or of the object that is positioned on the patient table. In this case, the monitoring unit can comprise a computing module and/or a processor in order to determine, in particular automatically and/or independently, an appropriate setting parameter with the aid of the acquired position data. In addition, the monitoring unit can also comprise appropriate software and/or computer programs for determining a setting parameter with the aid of the acquired position data with the result that the monitoring unit is designed so as to automatically provide a setting parameter for setting the position of the patient table and/or of the object that is positioned on the patient table with the aid of position data that is acquired by means of the position acquisition unit, in particular by means of the camera.

Alternatively or in addition, the monitoring unit can also comprise a user interface for manually providing a setting parameter for setting the position of the patient table and/or of the object that is positioned on the patient table. In this case, it is possible using the user interface, in particular an output unit of the user interface, to output the acquired position data to a user. Setting parameters for setting a position of the patient table and/or of the object that is positioned on the patient table can be input in this case with the aid of the illustrated position data by means of an input unit of the user interface.

The aspects of the disclosure render it advantageously possible to provide a simple and rapid positioning of the patient table and/or of the object that is positioned and/or arranged on the patient table in the reference position. In addition, it is possible in so doing to monitor and/or check a positioning of the patient table and/or of the object that is positioned and/or arranged on the patient table in the reference position. By means of the position acquisition unit, in particular by means of the camera, in addition a continuous monitoring is possible, for example by means of a video stream, which is transmitted to the monitoring unit and is output, for example, to a user, which in addition renders possible a simple and rapid setting of a position of the patient table and/or of the object that is positioned on the patient table.

In addition, it is possible by means of the position acquisition unit, in particular by means of the camera, to monitor further a positioning of the patient table within the patient receiving region and consequently to achieve a high safety standard during the positioning of the patient table. For example, it is possible in this manner while moving the patient table into the patient receiving region to identify parts, for example cables or an arm of the patient, which are overhanging from the patient table, and stop and/or pause the positioning procedure.

In one advantageous embodiment of the system in accordance with the disclosure, it is possible to provide that the magnetic resonance apparatus comprises an interface module that has an interface and is designed so as to establish a connection to an interface module of the monitoring unit, and the monitoring unit comprises an external user interface, having:
an interface module that has an interface and is designed so as to establish a connection to the interface module of the magnetic resonance apparatus,
an output unit that is designed so as to output the position data, and
an input unit that is designed so as to input a setting parameter for setting a positioning of the patient table and/or of the object that is positioned on the patient table.

It is preferred that the magnetic resonance apparatus comprises an internal user interface which comprises in particular an input unit, for example a keyboard and/or a touch screen, and an output unit, such as for example a monitor and/or a display and/or a touch display. The internal interface is permanently connected in one operational mode of the magnetic resonance apparatus to a control unit and/or to further units of the magnetic resonance apparatus, with the result that a user can always use the internal user interface without having to provide in advance a connection, in particular a data connection, to the magnetic resonance apparatus, in particular to the control unit of the magnetic resonance apparatus.

In contrast, the interface module is designed so as to establish a connection, in particular a data connection, to an external user interface. The external user interface enables a user who is not at the site of the magnetic resonance apparatus to exchange information and/or data with the magnetic resonance apparatus. In this case, the external user interface can be arranged outside a building in which the magnetic resonance apparatus is arranged. In order to exchange data with the magnetic resonance apparatus, the user must for this purpose initially establish and/or produce a connection, in particular a data connection, between the external user interface and the magnetic resonance apparatus. The external user interface has for this purpose likewise an interface module having an interface. For establishing a data connection, it is preferred that connection-establishing data, for example access data, etc. is exchanged between the interface module of the magnetic resonance apparatus and the interface module of the external user interface. It is preferred that the external user interface has an output unit which comprises in particular a monitor or a display for outputting position data that is acquired by means of the position acquisition unit, and an input unit, for example a touch display, a keyboard and/or a computer mouse, etc. In addition, the external user interface can comprise further units, such as for example a processor and/or a storage unit, etc.

By virtue of this embodiment of the disclosure, a procedure of positioning the patient table can be advantageously monitored and/or controlled from the external user interface by an expert and/or by a user who is experienced in positioning procedures. In particular, such an approach renders it possible to save time in comparison to when the patient table is positioned by an inexperienced user on site. A further advantage is that an inexperienced and/or untrained member of staff is also advantageously assisted in the preparation and/or performance of a magnetic resonance apparatus.

In one advantageous development of the system in accordance with the disclosure, it is possible to provide that the scanner unit comprises a front side and a rear side with respectively one insertion opening for the patient receiving region, and the position acquisition unit is arranged on the front side and/or on the rear side of the scanner unit above the insertion opening. Preferably, the position acquisition unit, in particular the camera, is arranged in this case in such a manner above the insertion opening that the field of view of the position acquisition unit, in particular of the camera, is oriented in a perpendicular manner downwards. This arrangement of the position acquisition unit has the advantage that the position acquisition unit, in particular the camera, has an uninterrupted view of the patient table and consequently also of the object that is positioned on the patient table in the reference position.

In one advantageous development of the system in accordance with the disclosure, it is possible to provide that the position acquisition unit, in particular the camera, has a data interface for connecting to the setting unit. It is preferred that the data interface comprises a universal data interface, such as for example a USB interface and/or an HDMI interface, etc. In this manner, the position acquisition unit can also be integrated retrospectively in particular in a simple manner into already existing magnetic resonance apparatuses so as to acquire position data of the patient table and/or of the object that is positioned on the patient table. In addition, it is possible in this manner to also use a conventional camera for acquiring the position data and consequently to provide a cost-effective position acquisition unit.

In one advantageous development of the system in accordance with the disclosure, it is possible to provide that the position acquisition unit has a marking element that is designed so as to mark a relevant region of the patient table and/or of the object that is positioned on the patient table. The marking element can comprise in this case a marking element, such as for example a crosshair, that is integrated into the optics of the position acquisition unit, in particular of the camera. In addition, the marking element can also comprise a marking element that is superimposed on the acquired position data. In addition, the marking element can also comprise a laser element that projects a marking, in particular a laser marking, directly onto the patient table and/or onto the object that is positioned on the patient table during acquisition of the position data by means of the position acquisition unit, in particular by means of the camera. In this manner, it is possible in a particularly simple manner to acquire a reference point for the subsequent positioning of the patient table and/or of the object that is positioned on the patient table within the patient receiving region, in particular within the isocenter of the magnetic resonance apparatus.

In one advantageous development of the system in accordance with the disclosure, it is possible to provide that the position acquisition unit, in particular the camera, has a calibration apparatus. The position acquisition unit, in particular the camera, is calibrated in particular during installation of the magnetic resonance apparatus and/or during installation of the position acquisition unit. In addition, the position acquisition unit, in particular the camera, can also be calibrated at regular time intervals in order to check the orientation of the position acquisition unit, in particular the camera. The calibration apparatus comprises, for example, a mirror that is positioned in a defined position on the patient table. In addition, the calibration apparatus can also comprise a laser marking. In this case, the camera is calibrated by a user, in particular an external user, by means of the user interface, in particular by means of the external user interface. In this manner, it is possible for a simple and rapid calibration to be performed by an experienced user and consequently accuracy of the position acquisition unit is also ensured.

Furthermore, the disclosure relates to a method for setting a position of patient table and/or an object that is positioned on the patient table in a system, comprising the following method steps:
S1: Acquiring position data of the patient table and/or of the object that is positioned on the patient table by means of a position acquisition unit of a magnetic resonance apparatus, wherein the position data comprises at least in part video data,
S2: Providing the acquired position data to a monitoring unit,
S3: Determining at least one setting parameter for setting a position of the patient table and/or of the object that is positioned on the patient table by means of the monitoring unit with the aid of the acquired position data,
S4: Providing the at least one setting parameter to a setting unit, and
S5: Setting the position of the patient table and/or of the object that is positioned on the patient table by means of the setting unit with the aid of the at least one provided setting parameter.

Providing the acquired position data can comprise transmitting the acquired position data from the position acquisition unit to the monitoring unit. Likewise, providing the at least one setting parameter comprises transmitting the at least one setting parameter from the monitoring unit to the setting unit. If the monitoring unit comprises an internal unit, in particular a unit comprised by the magnetic resonance apparatus, providing the acquired position data can involve transmitting data from the position acquisition unit to the monitoring unit by means of an internal, already existing data connection of the magnetic resonance apparatus. In addition, providing the at least one setting parameter can involve transmitting data from the monitoring unit to the setting unit by means of an internal, already existing data connection of the magnetic resonance apparatus.

If, on the other hand, the monitoring unit comprises an external unit, in particular an external user interface, a data connection between the magnetic resonance apparatus, for example a control unit of the magnetic resonance apparatus, and the external user interface is required for providing, in particular transmitting, the position data. It is also necessary for providing the at least one setting parameter to provide a data connection between the magnetic resonance apparatus, for example a control unit of the magnetic resonance apparatus, and the external user interface. For this purpose, it is preferred that the external user interface and also the magnetic resonance apparatus have a corresponding interface module in order to establish the data connection between the magnetic resonance apparatus and the external user interface.

By virtue of the method in accordance with the disclosure, a procedure of positioning the patient table can be advantageously monitored and/or controlled from the external user interface by an expert and/or a user who is experienced in positioning procedures. In particular, such an approach renders it possible to save time in comparison to when the patient table is positioned by an inexperienced user on site. A further advantage is that an inexperienced and/or untrained member of staff is also advantageously assisted in the preparation and/or performance of a magnetic resonance apparatus.

In addition, it is advantageously possible to provide a simple and rapid positioning of the patient table and/or of the object that is positioned and/or arranged on the patient table in the reference position. In addition, it is possible in this case to monitor and/or check a positioning of the patient table and/or of the object that is positioned and/or arranged on the patient table in the reference position. By means of the position acquisition unit, in particular the camera, in addition a continuous monitoring is possible, for example by means of a video stream, which is transmitted to the monitoring unit and is output, for example, to a user, which in addition renders possible a simple and rapid setting of a position of the patient table and/or of the object that is positioned on the patient table.

In addition, it is possible by means of the position acquisition unit, in particular by means of the camera, to monitor further a positioning of the patient table within the patient receiving region and consequently to achieve a high safety standard during the positioning of the patient table. For example, it is possible in this manner while moving the patient table into the patient receiving region to identify parts, for example cables or an arm of the patient, which are overhanging from the patient table, and stop and/or pause the positioning procedure.

The advantages of the method in accordance with the disclosure for setting a position of a patient table and/or of an object that is positioned on the patient table correspond essentially to the advantages of the system in accordance with the disclosure, which are disclosed in detail above. In this case, mentioned features, advantages or alternative embodiments can likewise also be transferred to the other claimed subjects and conversely.

In one advantageous development of the method in accordance with the disclosure, it is possible to provide that the method steps S1 to S5 are repeated until the patient table and/or the object that is positioned on the patient table is arranged in a reference position. The reference position has a defined and/or predetermined distance from the isocenter of the magnetic resonance apparatus. For the positioning of the patient table and/or of the object that is to be examined, in particular, a region of the patient table and/or of the object that is positioned on the patient table that is relevant for the imminent examination is positioned in this reference position. This relevant region of the patient table and/or of the object that is positioned on the patient table can also be identified in addition by a marking which is arranged in the relevant region on the patient table and/or on the object that is positioned on the patient table.

This embodiment of the disclosure has the advantage that a positioning procedure for the positioning of the patient table and/or of the object that is positioned on the patient table can be directly monitored, in particular monitored externally. In addition, targeted countermeasures can be taken in the event of undesirable movements of the patient table, for example by selecting appropriate setting parameters.

In one advantageous development of the method in accordance with the disclosure, it is possible to provide that, during an entire procedure of moving the patient table into the patient receiving region, position data can be acquired by the position acquisition unit and can be provided to the monitoring unit. Consequently, the procedure of moving in the patient table can be advantageously monitored until said patient table is arranged in its target position within the isocenter of the magnetic resonance apparatus. In particular, it is possible in this manner to monitor the moving-in procedure automatically by means of the monitoring unit and/or manually by a user by means of the monitoring unit and in so doing possible dangers, such as for example overhanging cables and/or an arm or a leg of the patient protruding over the patient positioning apparatus etc. can be identified. This renders it possible in a dangerous situation to stop the movement of the patient table and/or to initiate further measures for eliminating the danger and consequently advantageously increase the safety for the patient during a magnetic resonance examination.

In one advantageous development of the method in accordance with the disclosure, it is possible to provide that the position acquisition unit is deactivated during a magnetic resonance measurement. This has the advantage that an undesired interaction between the position acquisition unit, in particular between the camera, and the magnetic resonance apparatus, in particular the high-frequency antenna unit, can be advantageously prevented. Consequently, the position acquisition unit, in particular the camera, can be arranged on the magnetic resonance apparatus, in particular on the scanner unit of the magnetic resonance apparatus, without special shielding and thus saving components and costs.

In one advantageous development of the method in accordance with the disclosure, it is possible to provide that the monitoring unit has a computing module that with the aid of the provided position data automatically and/or independently determines the at least one setting parameter. The monitoring unit can comprise in this case a computing module and/or a processor. Thus, the monitoring unit can be designed so as to execute computer-readable instructions. In particular, the monitoring unit can comprise a storage unit, wherein computer-readable information is stored on the storage unit, wherein the monitoring unit is designed so as to load the computer-readable information from the storage unit and execute the computer-readable information. The components of the monitoring unit can be designed predominantly in the form of software components. In principle, these components can, however, also in part be implemented in the form of software-supported hardware components, for example FPGAs or the like, especially when particularly fast calculations are involved. Likewise, the required interfaces can be designed as software interfaces, for example if only a transfer of data from other software components is involved. However, they can also be designed as hardware interfaces that are controlled by suitable software. Of course, it is also conceivable that several of the components mentioned are implemented together in the form of a single software component or a software-supported hardware component.

In this manner, it advantageously possible to provide a rapid and automatic positioning of the patient table and/or of the object that is positioned on the patient table. This can be of advantage especially when performing measurements using phantoms.

In one advantageous development of the method in accordance with the disclosure, it is possible to provide that the monitoring unit comprises an external user interface having an interface module, wherein the interface module forms a data connection with the magnetic resonance apparatus so as to transmit the position data and/or the at least one setting parameter.

By virtue of this embodiment of the disclosure, a procedure of positioning the patient table can be advantageously monitored and/or checked from the external user interface by an expert and/or by a user who is experienced in positioning procedures, in particular an external user. In particular, such an approach renders it possible to save time in comparison to when positioning the patient table is performed by an inexperienced user on site and consequently it is also possible to assist an inexperienced member of staff.

Furthermore, the disclosure is based on a non-transitory computer-readable program product, which comprises a program and is loadable directly into a storage device of a programmable control unit, having a program in order to control a method for setting a position of a patient table and/or of the object that is positioned on the patient table if the program is executed in the control unit. In this case, the computer program potentially requires program means, for example, libraries and auxiliary functions, in order to implement the corresponding embodiments of the method. The computer program can in this case comprise software having a source code which still has to be compiled and linked or which only has to be interpreted, or an executable software code which only has to be loaded into an appropriate computing unit for execution.

The computer program product in accordance with the disclosure can be loaded directly into a storage device of a programmable computing unit and/or control unit and has program code means in order to perform a method in accordance with the disclosure if the computer program product is executed in the computer unit and/or control unit. The computer program product can be a computer program or can comprise a computer program. As a result, the method in accordance with the disclosure can be performed rapidly, repeatably identically and in a robust manner. The computer program product is configured in such a manner that it can perform the method steps in accordance with the disclosure by means of the computing unit and/or control unit. The computing unit and/or control unit must in this case have respectively the prerequisites, such as for example an appropriate working storage device, an appropriate graphics card or an appropriate logic unit, so that the respective method steps can be performed efficiently. The computer program product is, for example, stored on a computer-readable medium or stored on a network or server, from where it can be loaded into the processor of a local computing unit and/or control unit, which can be directly connected to the magnetic resonance apparatus or can be designed as a part. Furthermore, control information of the computer program product can be stored on an electronically readable data carrier. The control information of the electronic readable data carrier can be configured in such a manner that when using the data carrier in a computing unit and/or in a control unit, said control information performs the method in accordance with the disclosure. Thus, the computer program product can also represent the electronically readable data carrier. Examples of electronically readable data carriers are a DVD, a magnetic tape, a hard drive or a USB stick, on which electronically readable control information, in particular software (cf. above), is stored. If this control information (software) is read from the data carrier and stored in a controller and/or a computing unit, all embodiments in accordance with the disclosure of the method described above can be performed. Thus, the disclosed aspects can also be based on the said computer-readable medium and/or the said electronically readable data carrier.

BRIEF DESCRIPTION OF THE DRAWINGS

Further advantages, features and details of the disclosure will become apparent from the exemplary embodiment described hereinbelow as well as with reference to the drawings.

In the drawings:

FIG. 1 shows a system in accordance with the disclosure having a magnetic resonance apparatus and a position acquisition unit in a schematic representation, FIG. 2 shows position data acquired by means of the position acquisition unit, FIG. 3 shows a calibration apparatus of the position acquisition unit, and FIG. 4 shows a method in accordance with the disclosure for setting a position of a patient table and/or of an object that is positioned on the patient table.

DETAILED DESCRIPTION

FIG. 1 illustrates schematically a system 10 having a magnetic resonance apparatus 11. The magnetic resonance apparatus 11 comprises a scanner unit 12 that is formed by a magnet unit. In addition, the magnetic resonance apparatus 11 has a patient receiving region 13 for receiving a patient 14. The patient receiving region 13 in the present exemplary embodiment is cylindrical in shape and is surrounded in a cylindrical manner in a peripheral direction by the scanner unit 12, in particular by the magnet unit. In principle, however, a different design of the patient receiving region 13 is conceivable at any time. The patient 14 can be pushed and/or moved by means of a patient positioning apparatus 15 of the magnetic resonance apparatus 11 into the patient receiving region 13. The patient positioning apparatus 15 has for this purpose a patient table 16 that is configured so as to be able to be moved within the patient receiving region 13. In particular, the patient table 16 is stored in this case in such a manner as to be able to be moved in the direction of a longitudinal extent of the patient receiving region 13 and/or in a Z-direction.

The scanner unit 12, in particular the magnet unit, comprises a super-conducting basic magnet 17 for generating a strong and in particular constant basic magnetic field 18. Furthermore, the scanner unit 12, in particular the magnet unit, has a gradient coil unit 19 for generating magnetic field gradients that are used for position encoding during imaging. The gradient coil unit 19 is controlled by means of a gradient control unit 20 of the magnetic resonance apparatus 11. The scanner unit 12, in particular the magnet unit, comprises furthermore a high-frequency antenna unit 21 for exciting a polarization that is produced in the basic magnetic field 18 that is generated by the basic magnet 17. The high-frequency antenna unit 21 is controlled by a high-frequency antenna control unit 22 of the magnetic resonance apparatus 11 and irradiates high-frequency magnetic resonance sequences into the patient receiving region 13 of the magnetic resonance apparatus 11.

In order to control the basic magnet 17, the gradient control unit 20 and so as to control the high-frequency antenna control unit 22, the magnetic resonance apparatus 11 has a system control unit 23. The system control unit 23 centrally controls the magnetic resonance apparatus 11, such as for example by performing a predetermined imaging gradient echo sequence. In addition, the system control unit 23 comprises an evaluation unit (not shown in detail) for evaluating medical image data that is acquired during the magnetic resonance examination.

Furthermore, the magnetic resonance apparatus 11 comprises an internal user interface 24 that is connected to the system control unit 23. Control information, such as for example imaging parameters, and also reconstruction magnetic resonance images can be displayed on an output unit 25, for example on at least one monitor, of the internal user interface 24 for a medical operator working on site at the magnetic resonance apparatus. Furthermore, the internal user interface 24 has an input unit 26, by means of which information and/or parameters are input by the medical operator during a measuring procedure. The internal user interface 24 of the magnetic resonance apparatus 11 is permanently connected to the system control unit 23 and/or further units of the magnetic resonance apparatus 11, with the result that the user can always use the internal user interface 24 without having to provide in advance a connection, in particular a data connection, to the magnetic resonance apparatus 11, in particular the control unit 23 of the magnetic resonance apparatus 11.

Furthermore, the magnetic resonance apparatus 11 has a position acquisition unit 27 which is designed so as to acquire position data of a position of the patient table 16 and/or of an object 28 that is positioned on the patient table 16 (FIG. 1). The object 28 that is positioned on the patient table 16 can be a patient 14, in particular a region of a patient 14 that is to be examined and/or a local high-frequency coil and/or a phantom, etc. The position acquisition unit 27 comprises a camera. The position acquisition unit 27, in particular the camera, is arranged on a front side 29 of the scanner unit 12. In particular, the camera is arranged above an insertion opening 30 of the patient receiving region 13 on the front side 29 of the scanner unit 12. The position acquisition unit 27, in particular the camera, has in this case a data interface 31 for a connection, in particular a data connection, to the system control unit 23 and/or to a setting unit 32 of the magnetic resonance apparatus 11. It is preferred that the data interface 31 comprises a universal data interface 31, such as for example a USB interface and/or an HDMI interface, etc. Alternatively, the position acquisition unit 27, in particular the camera, can also be arranged on a rear side of the scanner unit 12, in particular above an insertion opening of the patient receiving region 13 on the rear side of the scanner unit 12.

The position acquisition unit 27, in particular the camera, has an acquisition region and/or a field of view 33 that is directed at a region directly in front of the insertion opening 30 (FIG. 1). The patient table 16 and/or the object 28 that is positioned on the patient table 16 is positioned for a positioning within the isocenter of the magnetic resonance apparatus 11 initially in a reference position which is preferably arranged in the field of view 33 of the camera. In particular, in this case a relevant point and/or a relevant region of the patient table 16 and/or of the object 28 that is positioned on the patient table 16 is positioned and/or arranged in this reference position. This relevant point and/or a relevant region of the patient table 16 and/or of the object 28 that is positioned on the patient table 16 is identified in the present exemplary embodiment by means of a marking element 34. The reference position has a defined distance from the isocenter of the magnetic resonance apparatus 11. In order to position the patient table 16 and/or the object 28 that is positioned on the patient table 16 in the reference position, position data is acquired by the position acquisition unit 27.

In order to acquire accurate position data, the position acquisition unit 27 has a marking element 35 that is designed so as to mark the relevant region of the patient table 16 and/or of the object 28 that is positioned on the patient table 16, as this is apparent in FIG. 2. FIG. 2 illustrates position data that is acquired by means of the position acquisition unit 27, in particular the camera. The marking element 35 of the position acquisition unit 27 is apparent in the position data. In addition, the patient table 16 with the patient 14 positioned on the patient table 16 is apparent. In this case, the marking element 35 of the position acquisition unit 27 can comprise a marking element 35, such as for example a crosshair, and said marking element is integrated into the optics of the position acquisition unit 27, in particular the camera. In addition, the marking element 35 of the position acquisition unit 27 can also comprise a marking element 35 that is superimposed on the position data. The marking element 35 of the position acquisition unit 27 can in addition also comprise a laser element that projects a marking, in particular a laser marking, directly onto the patient table 16 and/or onto the object 28 that is positioned on the patient table 16.

The position acquisition unit 27, in particular the camera, has in addition a calibration apparatus 36 (FIG. 3). The calibration apparatus 36 comprises in the present exemplary embodiment for example a mirror that is positioned for calibrating the position acquisition unit 27, in particular the camera, in a defined position on the patient table 16. In addition, the calibration apparatus 36 can also comprise a laser marking. In this case, the position acquisition unit 27, in particular the camera, is calibrated with the aid of reflected optics, in particular a lens, of the camera. In this case, the reflected optics, in particular a center of the lens, should coincide with the marking element 35 of the camera.

The magnetic resonance apparatus 11 has in addition a setting unit 32 that is designed so as, with the aid of a provided setting parameter, to set the position of the patient table 16 and/or of the object 28 that is positioned on the patient table (FIG. 1). It is preferred that the setting unit 32 has for this purpose a drive unit (not illustrated in detail) which generates a drive torque for a movement of the patient table 16. In addition, the setting unit 32 can also comprise a computing module and/or a processor in order to control a movement of the patient table 16 and consequently also a positioning of the patient table 16. Furthermore, the setting unit 32 can also comprise appropriate software and/or computer programs for controlling a movement and/or positioning of the patient table 16.

Furthermore, the system 10 comprises a monitoring unit 37 that is designed so as, with the aid of the acquired position data, to provide a setting parameter for setting the position of the patient table 16 and/or of the object 28 that is positioned on the patient table 16. It is preferred that the monitoring unit 37 comprises a computing module and/or a processor in order to determine an appropriate setting parameter with the aid of the acquired position data. The computing module and/or the processor is preferably comprised by the magnetic resonance apparatus 11. In addition, the monitoring unit 37 can also comprise appropriate software and/or computer programs for determining a setting parameter with the aid of the acquired position data, with the result that the monitoring unit 37 is designed so as to automatically provide a setting parameter for setting the position of the patient table 16 and/or of the object 28 that is positioned on the patient table 16.

The monitoring unit 37 comprises furthermore an external user interface 38 (FIG. 1), wherein the external user interface 38 comprises an output unit 39. It is possible by means of the output unit 38 for an external user to output position data that is acquired by means of the position acquisition unit 27. In addition, the external user interface 38 comprises an input unit 40. It is possible by means of the input unit 40 for an external user to input setting parameters for setting a position of the patient table 16 and/or of the object 28 that is positioned on the patient table 16. Furthermore, the external user interface 38 comprises an interface module 41 having an interface 42, which is designed so as to establish a connection, in particular a data connection, to the magnetic resonance apparatus 11. Likewise, the magnetic resonance apparatus 11 also has for this purpose an interface module 43 having an interface 44, wherein the interface 44 is designed so as to establish a connection, in particular a data connection to the interface module 41 of the external user interface 38.

The illustrated magnetic resonance apparatus 11 can of course comprise further components that magnetic resonance apparatuses 11 usually have. A general mode of functioning of a magnetic resonance apparatus 11 is in addition known to the person skilled in the art and so a detailed description of the further components is omitted.

FIG. 4 illustrates a method in accordance with the disclosure for setting a position of the patient table 16 and/or of the object 28 that is positioned on the patient table 16. The method is performed by means of the system 10 having the magnetic resonance apparatus 11 and the monitoring unit 37. In addition, the method is controlled by a control unit 45 of the magnetic resonance apparatus 11, wherein the control unit 45 has for this purpose a computing module and/or a processor. In addition, the control unit 45 comprises appropriate control programs and/or control software which, on execution, is designed to control a setting of a position of a patient table 16 and/or of an object 28 that is positioned on the patient table 16. The control unit 45 can be comprised in this case by the setting unit 32 and/or the system control unit 23. In addition, it is also conceivable that the control unit 45 is designed separately to the setting unit 32 and/or the system control unit 23.

At the start of the method, the object 28 is already positioned on the patient table 16. The object 28 can comprise, for example, the patient 14 who is positioned for a magnetic resonance examination on the patient table 16. In addition, the object 28 can also comprise a local high-frequency coil that, for the acquisition of magnetic resonance data, is arranged around the region of the patient 14 that is to be examined. Furthermore, the object 28 can comprise a phantom for example, for a calibration measurement, etc., which is arranged in a defined position on the patient table 16. In addition a region, that is relevant for the imminent measurement, of the patient table 16 and/or of the object 28 that is positioned on the patient table 16 can also be identified using the marking element 34.

In this case, in a first method step S1 position data of the patient table 16 and/or of the object 28 that is positioned on the patient table 16 is acquired by means of the position acquisition unit 27, in particular the camera. The acquired position data comprises in this case video data. It is preferred that in so doing position data, in particular video data, is acquired during the entire procedure of positioning the patient table 16 and/or the object 28 that is positioned on the patient table 16. In particular, in so doing position data from the reference position is acquired and by means of the position data a position of a region, which is relevant and/or is marked by means of the marking element 34, of the patient table 16 and/or of the object 28 that is positioned on the patient table 16 in the environment and/or within the reference position is determined.

The acquired position data is provided to the monitoring unit 37 in a second method step S2 that follows on from the first method step S1. Providing the position data can in this case comprise providing the position data to a computing module of the monitoring unit 37. In this case, providing a data transmission from the position acquisition unit 27 to the monitoring unit 37, in particular to the computing module, can be performed by means of an internal data transmission unit of the magnetic resonance apparatus 11. In addition, providing the position data can also comprise providing it to the external user interface 38 of the monitoring unit 37. In this case, the providing can also involve producing and/or establishing a connection, in particular a data connection to the external user interface 38 and a data transmission to the external user interface 38. It is preferred that providing the position data to the external user interface 38 also comprises a representation and/or display of the position data on the output unit of the external user interface 38. In particular, an external user can in this manner view a video for the positioning of the patient table 16 and/or of the object 28 that is positioned on the patient table 16.

In a subsequent third method step S3, at least one setting parameter for setting the position of the patient table 16 and/or of the object 28 that is positioned on the patient table 16 is determined with the aid of the acquired and provided position data. If the monitoring unit 37 comprises an external user interface 38, which is currently connected to the magnetic resonance apparatus 11 via the interface module 41, 43, an external user selects with the aid of the position data, in particular by means of the input unit 40, at least one setting parameter on the external user interface 38 for setting the position of the patient table 16 and/or of the object 28 that is positioned on the patient table 16. If, on the other hand, there is no connection to the external user interface 38, it is possible with the aid of the provided position data for the at least one setting parameter to be determined and/or defined automatically and/or independently by the computing module of the monitoring unit 37.

In a further method step S4, the at least one setting parameter is provided to the setting unit 32 of the magnetic resonance apparatus 11. In this case, providing the at least one setting parameter can involve transmitting the at least one setting parameter from the monitoring unit 37, in particular the computing module of the monitoring unit 37, to the setting unit 32 by means of an internal data transmission unit of the magnetic resonance apparatus 11. In addition, providing the at least one setting parameter to the setting unit 32 can also involve transmitting the at least one setting parameter from the external user interface 38 of the monitoring unit 37 to the setting unit 32 by means of the data connection that has been established by the two interface modules 41, 43.

In a fifth method step S5, the position of the patient table 16 and/or of the object 28 that is positioned on the patient table 16 is then set by means of the setting unit 32 with the aid of the provided setting parameter.

Here, the method steps S1 to S5 are repeated until the relevant region and/or the region of the patient table 16 and/or of the object 28 that is positioned on the patient table 16 which is marked by means of the marking element 34 is arranged and/or positioned in the correct reference position.

In addition, it is possible after positioning the patient table 16 and/or the object 28 that is positioned on the patient table 16 to continue to acquire position data of the patient table 16 and/or of the object 28 that is positioned on the patient table 16 in a further method step S6 by means of the position acquisition unit 27, in particular the camera, until the patient table 16 and/or the object 28 that is positioned on the patient table 16 is arranged in the isocenter of the magnetic resonance apparatus 11. This position data that is acquired in the further method step S6 is likewise provided to the monitoring unit 37 with the result that the entire procedure of moving-in and/or the entire procedure of positioning the patient table 16 into the patient receiving region 13, in particular into the isocenter of the magnetic resonance apparatus 11, can be monitored and checked. In this manner it is possible, for example by means of the monitoring unit 37, to identify objects hanging down from the patient table 16, such as for example cables etc. In such a case, it is possible to stop a movement of the patient table 16 immediately, for example by a manual stop by means of the input unit 40 of the external user interface 38 or an automatic stop by means of the computing module of the monitoring unit 37.

After a positioning of the patient table 16 and/or the object 28 that is positioned on the patient table 16 within the patient receiving region 13, in particular within the isocenter of the magnetic resonance apparatus 11, the position acquisition unit 27, in particular the camera, is deactivated in a further, seventh method step S7. In addition, the position detection unit 27, in particular the camera, can already be deactivated in the method step S7 as soon as the patient table 16 and/or the object 28 that is positioned on the patient table 16 is arranged and/or positioned within the reference position.

Although the aspects of the disclosure have been illustrated and described in detail with the preferred exemplary embodiment, the invention is not restricted by the examples given, and a person skilled in the art can derive other variations therefrom without departing from the protective scope of the invention.

The invention claimed is:

1. A system comprising a magnetic resonance apparatus and a monitoring unit, wherein the magnetic resonance apparatus comprises:
 a scanner unit operable to acquire medical magnetic resonance data;
 a patient receiving region that is surrounded at least in part by the scanner unit;
 a patient positioning apparatus having a movable patient table, wherein the patient table is movable into the patient receiving region;
 a position detection unit operable to acquire position data of a position of the patient table and/or of an object that is positioned on the patient table with respect to a reference position and/or in relation to an isocenter of the scanner unit, wherein the position detection unit comprises a camera;
 an adjustment unit operable to adjust the position of the patient table and/or of the object that is positioned on the patient table based on a provided adjustment parameter,
 wherein the monitoring unit is operable to provide the adjustment parameter for adjusting the position of the patient table and/or of the object that is positioned on the patient table based on the acquired position data;
 an internal user interface comprising an input unit and an output unit, wherein the internal user interface is permanently connected to a control unit in an operating mode of the magnetic resonance apparatus and/or other units of the magnetic resonance apparatus,
 wherein the monitoring unit comprises an external user interface with an interface module that has an interface and is designed to establish a connection with an interface module of the magnetic resonance apparatus, wherein for data exchange with the magnetic resonance apparatus the user must establish a data connection between the external user interface and the magnetic resonance apparatus.

2. The system as claimed in claim 1,
wherein the magnetic resonance apparatus comprises an interface module that has an interface and is operable to establish a connection to an interface module of the monitoring unit, and
wherein the external user interface of the monitoring unit comprises:
an output unit operable to output the position data; and
an input unit operable to input the adjustment parameter to adjust the position of the patient table and/or of the object that is positioned on the patient table.

3. The system as claimed in claim 1,
wherein the scanner unit comprises a front side and a rear side with respectively, one insertion opening for the patient receiving region, and the position detection unit is arranged on the front side and/or on the rear side of the scanner unit above the insertion opening.

4. The system as claimed in claim 1,
wherein the position detection unit has a data interface operable to connect to the adjustment unit.

5. The system as claimed in claim 1,
wherein the position detection unit has a marking element operable to mark a relevant region of the patient table and/or of the object that is positioned on the patient table.

6. The system as claimed in claim 1,
wherein the camera has a calibration apparatus.

7. A method for adjusting a position of a patient table and/or of an object that is positioned on the patient table in a system that is designed as claimed in claim 1, the method comprising:
S1: acquiring position data of the patient table and/or of the object that is positioned on the patient table using a position detection unit of a magnetic resonance apparatus, wherein the position data comprises video data;
S2: providing the acquired position data to a monitoring unit;
S3: determining at least one adjustment parameter for adjusting a position of the patient table and/or of the object that is positioned on the patient table using the monitoring unit with the acquired position data;
S4: providing the at least one adjustment parameter to an adjustment unit; and
S5: adjusting the position of the patient table and/or of the object that is positioned on the patient table using the adjustment unit with the at least one provided adjustment parameter.

8. The method as claimed in claim 7, further comprising:
repeating the method steps S1 to S5 until the patient table and/or the object that is positioned on the patient table is arranged in the reference position.

9. The method as claimed in claim 7, further comprising:
during an entire procedure of moving the patient table into the patient receiving region, acquiring position data by the position detection unit and providing the position data to the monitoring unit.

10. The method as claimed in claim 7, further comprising:
deactivating the position detection unit during a magnetic resonance measurement.

11. The method as claimed in claim 7,
wherein the monitoring unit has a computing module that with the provided position data automatically and/or independently determines the at least one adjustment parameter.

12. The method as claimed in claim 7,
wherein the monitoring unit comprises an external user interface having an interface module, wherein the interface module forms a data connection with the magnetic resonance apparatus so as to transmit the position data and/or the at least one adjustment parameter.

13. A non-transitory computer-readable program product, which comprises a program and can be loaded directly into a storage device of a programmable control unit, having a program to control a method for adjusting a position of a patient table and/or of an object that is positioned on the patient table as claimed in claim 7 when the program is executed in the control unit.

* * * * *